United States Patent [19]

Rapoport et al.

[11] Patent Number: 4,618,710
[45] Date of Patent: Oct. 21, 1986

[54] PREPARATION OF OPTICALLY ACTIVE KETONES

[75] Inventors: Henry Rapoport, Berkeley; Thomas F. Buckley, III, Albany, both of Calif.

[73] Assignee: The Regents of the University of Calif., Berkeley, Calif.

[21] Appl. No.: 417,771

[22] Filed: Sep. 13, 1982

Related U.S. Application Data

[62] Division of Ser. No. 262,972, May 12, 1981, abandoned.

[51] Int. Cl.$^4$ ............... C07C 125/065; C07C 125/067; C07C 143/74; C07C 143/78
[52] U.S. Cl. ........................................ 564/1; 564/94; 564/98; 558/144; 558/178; 556/76; 556/80; 560/24; 560/27; 560/32; 560/157; 560/163
[58] Field of Search ................... 560/30, 161, 27, 32, 560/24, 157, 163; 260/546; 564/102, 1, 94, 98; 558/144, 178; 556/76, 80

[56] References Cited

PUBLICATIONS

McOmie, Protective Groups in Organic Chemistry (1973) 43, 44, 55–61 & 71–75.
Jorgenson, Organic Reactions, vol. 18 (1970), pp. 1–13, 31–32, 39–53, 72–77, 82 and 84.

*Primary Examiner*—Bernard Helfin
*Attorney, Agent, or Firm*—Fliesler, Dubb, Meyer & Lovejoy

[57] ABSTRACT

An optically active alpha-amino acid derivative having the formula:

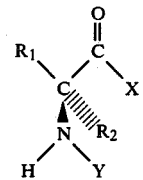

wherein:

X is OH, Cl, Br, I, or $OCOR_3$;

Y is a radical selected to stabilize the alpha carbon atom of the alpha-amino acid derivative sufficiently to prevent significant change in symmetry thereof during replacement of X with an alkyl, aryl, alkenyl, alkynyl, alkaryl, aralkyl, alkenaryl or alkynaryl radical, or such radical having one or more chemical constituents thereon; and $R_1$ and $R_2$ are different from one another and are each hydrogen or an alkyl, aryl, alkenyl, alkynyl, alkaryl, aralkyl, alkenaryl, or alkynaryl radical, or such radical having one or more non-protic chemical constituents thereon is conventionally synthesized from the corresponding alpha-amino acid. The

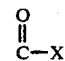

portion of the above derivative is converted to a ketone functionality without racemization.

8 Claims, No Drawings

PREPARATION OF OPTICALLY ACTIVE KETONES

This is a division of Ser. No. 262,972, filed May 12, 1981 and now abandoned.

DESCRIPTION

1. Technical Field

This invention relates to an optically active alpha-amino acid derivative and a method of converting the derivative to a ketone. The reaction takes place without racemization.

2. Background Art

Such biologically significant compounds as ephedrines, pseudoephedrines and amphetamines are optically active and are used quite widely as medicinals. In the past, it has been customary to synthesize racemic mixtures of such compounds and then to resolve the racemic mixtures into the desired optical isomers. Such optical resolution procedures are generally costly and inefficient. The provision of compounds convertible into, and methods for converting relatively inexpensive optically pure compounds into, optically pure biologically significant compounds would thus be highly desirable.

The present invention is directed to overcoming one or more of the problems as set forth above.

3. Disclosure of the Invention

In one aspect of the present invention, an optically active alpha-amino acid derivative is disclosed having the formula:

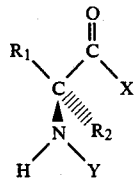

wherein:
X is OH, Cl, Br, I or

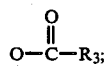

Y is a radical selected to stabilize the alpha carbon of the alpha amino acid derivative sufficiently to prevent significant change in symmetry thereof during replacement of X with alkyl, aryl, alkenyl, alkynyl, alkaryl, aralkyl, alkenaryl or alkynaryl radical or such a radical having one or more chemical constituents thereon;

$R_1$ and $R_2$ are different from one another and are each hydrogen, or an alkyl, aryl, alkenyl, alkynyl, alkaryl, aralkyl, alkenaryl, or alkynaryl radical, or such radical having one or more non-protic chemical constituents thereon; and $R_3$ is hydrogen, or an alkyl, aryl, alkenyl, alkynyl, alkaryl, aralkyl, alkenaryl or alkynaryl radical or such a radical having one or more chemical constituents thereon.

In accordance with another embodiment, the present invention is directed to a method of preparing an alpha-amino organic ketone which comprises reacting a compound as set out above with a reagent capable of converting the

portion of the compound to a ketone.

In essence, one, but not both, of the two hydrogens on the amine group of an alpha-amino acid is converted to a blocking group (Y). Thereafter, the acid portion of the alpha-amino acid is converted to a ketone through use of the Friedel-Crafts acylation reaction or by reaction with an organometallic compound, such as an organolithium compound, or by reaction with a Grignard reagent. The asymmetry of the alpha carbon is substantially retained. As a result, it is not necessary to carry out any resolution reaction on the product. The ketones can then be converted, as by mild reduction, to desired medicinal reagents, such as optically active ephedrines, pseudoephedrines and amphetamines, again with retention of asymmetry.

BEST MODE FOR CARRYING OUT THE INVENTION

In accordance with the present invention, it has been discovered that a particular class of optically active alpha-amino acid derivatives can have the acid group thereof converted to a ketone functionality with essentially complete retention of optical activity at the asymmetric alpha carbon atom. The optically active alpha-amino acid derivative can be represented by the formula:

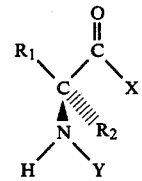

wherein:
X is OH, Cl, Br, I or

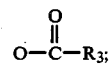

Y is a radical selected to stabilize the alpha carbon of the alpha-amino acid derivative sufficiently to prevent significant change in symmetry thereof during replacement of X with an alkyl, aryl, alkenyl, alkynyl, alkaryl, aralkyl, alkenaryl or alkynaryl radical having one or more chemical constituents thereon;

$R_1$ and $R_2$ are different from one another and are each hydrogen, or an alkyl, aryl, alkenyl, alkynyl, alkaryl, aralkyl, alkenaryl, or alyknaryl radical, or such a radical having one or more non-protic chemical constituents thereon; and $R_3$ is hydrogen, or an alkyl, aryl, alkenyl, alkynyl, alkaryl, aralkyl, alkenaryl or alkynaryl radical or such a radical having one or more chemical constituents thereon.

More particularly, Y is preferably

—$SO_2R_4$; —$SeO_2R_4$; —$TeO_2R_4$; —$PO_3R_4$;

-continued

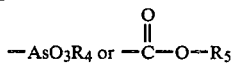

wherein
R₄ is hydrogen or an alkyl, aryl, alkenyl, alkynyl, alkaryl, aralkyl, alkenaryl, alkynaryl radical or such radical having one or more non-protic chemical constituents thereon, or is one or more non-protic chemical constituents; and R₅ is an alkyl, aryl, alkenyl, alkynyl, alkaryl,aralky, alkenaryl or alkynaryl radical or such radical having one or more non-protic chemical constituents. Most preferably, Y is:

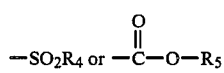

It has been discovered that the desired reactions occur if the blocking group, Y, is

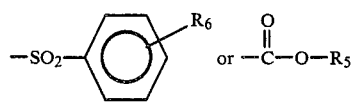

wherein
R₆ is hydrogen or an alkyl, aryl, alkenyl, alkynyl, alkaryl, aralklyl, alkenaryl, alkynaryl radical or an alkylene, alkenylene, alkarylene, alkenarylene, alkynarylene or arylene diradical, or such radical or diradical having one or more non-protic chemical constituents thereon, or is one or more non-protic chemical constituents. Particularly good results have been obtained when R₅ is C₂H₅ and R₆ is hydrogen or methyl.

Racemization of alpha-amino acid derivatives during ketone formation is only a problem when either R₁ or R₂ is hydrogen, but the reactions considered herein are operational even when neither R₁ nor R₂ is hydrogen. Generally, however, it will not be economically advantageous to utilize the method and alpha-amino acid derivative set out herein if neither R₁ nor R₂ is hydrogen.

The group X is either hydroxide, chloride, bromide, iodide or anhydride. Generally, the anhydride would be the anhydride of the same alpha-amino acid, although such is not essential. The particular X group chosen depends upon the reactant which is to be used to convert the alpha-amino acid derivative to a ketone. When the alpha-amino acid derivative is to be converted to a ketone by Friedel-Crafts acylation, the X group is chloride, bromide, iodide or anhydride. That is, the hydroxide does not allow the Friedel-Crafts acylation reaction to proceed to the desired product.

If the ketone is to be formed through reaction with an organolithium compound, it is best that the X group be a hydroxide, although the chloride, bromide, iodide and anhydride also work.

When a Grignard reagent is to be used to convert the acid function to a ketone function, the X group is preferably the chloride, although the hydroxide, bromide, iodide and anhydride are also useful.

It will be noted that when the ketone creating reaction is a Friedel-Crafts reaction, the resulting ketone formed must be aromatic, i.e., aryl or alkaryl or alkenaryl. When the ketone is created by reaction with an organometallic reagent such as organolithium or a Grignard reagent, then the ketone formed may include substantially any organic radical.

The alpha-amino acids which form the novel optically active alpha-amino acid derivative of the present invention include virtually all alpha-amino acids. For example, the alpha-amino acid may be phenylalaline, alanine, tryptophan, leucine, isoleucine, lysine, methionine, threonine, valine, arginine, histidine, glutamic acid, tyrosine, serine, or cysteine. In the case of alpha-amino acids which normally have other protic groups in addition to the hydrogens on the alpha-amino nitrogen and in the acid function, the other protic hydrogens must be replaced through esterification, or other blocking reaction, which changes the protic groups to non-protic groups. For example, histidine and arginine have additional NH hydrogens which must be replaced with non-protic groups. Serine, tyrosine and threonine have other OH groups which must be converted to non-protic groups. Cysteine has an SH group which must be converted to a non-protic group.

When the Freidel-Crafts reaction is used to convert the optically active alpha-amino acid derivative to a ketone, the aromatic compound, for example, benzene, which is to be added, should be used in an approximate ten-fold excess so as to promote highest product yield. However, some yield is obtained even when the benzene is only present in a stoichiometric amount. A Lewis acid catalyst is also present as in any Friedel-Crafts reaction, with aluminum chloride being the preferred catalyst. It is preferred that the reaction be under relatively mild conditions so as to avoid side reactions with concurrent loss of product.

When organolithium compounds are utilized to convert the optically active alpha-amino acid derivative into a ketone, it has been found that it is necessary that at least about 300 mol percent of the organolithium reagent is required for a high yield preparation. Low temperatures are also required during the addition of the organolithium reagent. Thereafter, warming is permissible up to about room temperature. If the organolithium compound is added initially at room temperature, significant side product formation results. Use of less than about 300 mol percent of the organolithium compound, likewise, leads to very significant production of side product. It is believed that timely extraction of the carbamate proton is critical to the reaction.

When Grignard reagent is used to convert the optically active alpha-amino derivative to a ketone, it has been found that a minimum of 200 mol percent of the Grignard reagent is needed. The reaction has been run by first adding 100 mol percent of the Grignard reagent. This led to the production of none of the desired ketone. The addition of a second 100 mol percent to the reaction mixture, however, afforded the desired product. It is believed that the first step involves an acid-based neutralization of the carbamate proton, thereby forming the oxazolinone. The second mol of Grignard is believed to then attack the oxazolinone carbonyl, leaving the ring system intact until aqueous hydrolysis liberates the ketone.

It is essential to the present invention that only one of the hydrogens on the alpho-amine group be blocked. That is, one hydrogen must remain attached to the amine nitrogen. The blocking group, i.e., the Y group of the formula set out above, is critical to successful practice of the present invention. When the ketone is to be formed by the Friedel-Crafts reaction, it is highly advantageous that the Y group be an ethoxycarbonyl group. Some product is obtained by the Friedel-Crafts reaction when the Y group is SO₂C₆H₅, but the yield is quite low. A slight yield is also obtained when the Y group is methoxycarbonyl, but the yield is again, basically, unsatisfactory.

When the ketone formation is attained through use of an organolithium reagent, the Y group may be ethoxycarbonyl, methoxycarbonyl, phenoxycarbonyl or the like, generally any compound of the formula $CO_2R_5$ where $R_5$ is as set out above. When organolithium is used to form the ketone the Y group may also be $SO_2R_4$, $SeO_2R_4$, $TeO_2R_4$, $PO_3R_4$ or $AsO_3R_4$, wherein $R_4$ is generally as previously set out. Generally, Y would be represented by the formula

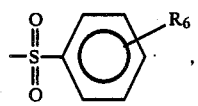

wherein $R_6$ is as previously set out.

The ketones formed by Friedel-Crafts or organometallic ketonization of the optically active alpha-amino acid derivative of the present invention can be reduced to medicinally active substances. For example, if the alpha-amino acid is alanine, the ketone can be reduced to an amphetamine, an ephedrine, or a pseudoephedrine. Generally, the conversion of the ketone takes place by relatively mild hydrogenation. Any of various reducing agents may be utilized. For example, sodium borohydride can be utilized in a solvent such as methanol, lithium aluminum hydride can be utilized in a solvent such as tetrahydrofuran, lithium selectride may be utilized in a solvent such as tetrahydrofuran, palladium catalyzed reduction carried out in a solvent such as ethanol, is likewise effective. The reaction products include ephedrine and pseudoephedrine and the ratio of the ephedrine to the pseudoephedrine is a function of the reducing agent selected. The ratio is approximately 4 to 1 when the reducing agent is sodium borohydride or lithium aluminum hydride, approximately 1 to 1 when the reducing agent is lithium selectride and approximately 2 to 1 when palladium catalyzed reduction takes place.

Reduction of S-2-ethoxycarbonylaminopropiophenone to ephedrine and pseudoephedrine is believed to take place via the equations:

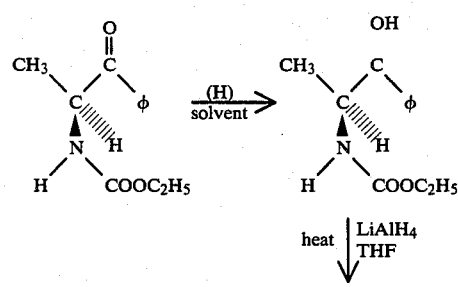

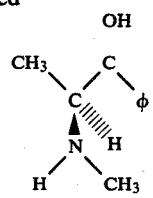

Reduction with either sodium borohydride or lithium aluminum hydride favored the erythro diastereomer ephedrine. No preference was found with lithium selectride, while catalytic hydrogenation in ethanol again favored the erythro diastereomer, but reduction occurred at a much slower rate. Partial cyclization of the hydroxy carbamate intermediate was observed during the catalytic hydrogenation.

The hydroxy carbamates obtained by catalytic hydrogenation were converted to a mixture of norephedrine and norpseudoephedrine by hydrolysis is hot aqueous methanolic potassium hydroxide. Reduction in the presence of 15%, volume per volume, of ethereal HCl in ethanol led to high yields of S-amphetamine carbamate. With all of the above reduction reactions, steric integrity was maintained, i.e., no racemization was detected.

The invention will be better understood by reference to the following experimental examples.

FRIEDEL-CRAFTS REACTIONS OF ACYL ALPHA-SECONDARY AMINO ACIDS WITH BENZENE

Example I

L-N-tosyl-N-methylalanine was prepared as described by Greenstein, J. P. and Winitz, M. in "Chemistry Of The Amino Acids", John Wiley & Sons, Inc., New York, 1961, Vol. III and was converted to the corresponding acid chloride. Upon addition of benzene and AlCl₃, the reaction mixture blackened and did not afford ketone. Considerable gas evolution was observed indicating that decarbamoylation was occurring.

This experiment showed the failure of the tosyl group to withstand Friedel-Crafts reaction condition.

Example II

L-N-Benzyloxycarbonyl-N-methylalanine was converted to its acid chloride via its sodium salt. Addition of benzene and AlCl₃ resulted in extensive decarbamoylation of the starting material, but, a trace of alpha-amino ketone was isolated as the free base. Immediate borohydride reduction produced a mixture of ephedrine and pseudoephedrine.

While this reaction demonstrated the production of the desired product from an alpha-secondary amino acid, the yield was so low as to be impractical.

Example III

The compound L-N-ethoxycarbonyl-N-methylalanine was converted to its acid chloride. Upon the addition of benzene and AlCl₃ decarbamoylation was again observed and N-methylalanine diketopiperazine was a major product.

The results of Examples I-III was to establish that acyl secondary amino acids are impractical candidates for the Lewis acid catalyzed acylation of non-activated aromatics.

FRIEDEL-CRAFTS REACTIONS OF ACYL ALPHA-PRIMARY AMINO ACIDS WITH BENZENE

Example IV

L-N-tosylalanine was converted to the corresponding acid chloride. Addition of benzene and AlCl$_3$ resulted in nearly quantative cleavage of the tosyl group, isolated as p-toluene sulphonic acid. The formation of alpha-amino ketone was not observed.

This example illustrates that the tosyl group is not useful when ketone is achieved via a Friedel-Crafts reaction.

Example V

L-N-benzyloxycarbonylalanine was converted to its acid chloride via its sodium salt. On addition of benzene and AlCl$_3$ the carbamoyl residue was lost.

This example illustrates that the benzyloxycarbonyl group is not useful when ketone formation is achieved via a Friedel-Crafts reaction.

Example VI

L-N-ethoxycarbonylalanine was directly converted to its acid chloride. Friedel-Crafts reaction with benzene and 200 mol percent AlCl$_3$ afforded a high yield of the desired ketone carbamate. The product was readily isolated and shown to be optically active.

This example, along with example III, illustrates the necessity that the nitrogen bear a proton and shows that the ethoxycarbonyl group is a useful blocking group when ketone formation is achieved via a Friedel-Crafts reaction.

ORGANOMETALLIC REACTIONS. REACTIONS OF N-ALKOXYCARBONYLALANINES WITH PHENYLLITHIUM

Example VII

Phenyllithium was added to L-N-ethoxycarbonylalanine and afforded the desired phenyl ketone in 85 to 90% yield. It was noted that at least 300 mol percent of the phenyllithium reagent was required for a high yield preparation. Low temperatures were necessary during the addition of the organolithium reagent. Warming was then permissible, however, product formation was delayed until the reaction temperature neared 0° C. Continued warming to room temperature facilitated ketone production. If phenyllithium was added at room temperature, significant amounts of ethyl benzoate were obtained. Also, ethyl benzoate was the chief product when 200 mol percent of phenyllithium was added to N-benzyl-N-ethoxycarbonylalanine.

Timely abstraction of the carbamate proton, thus, seems to be critical to this reaction. It is believed that the reaction proceeds as shown in the following equations:

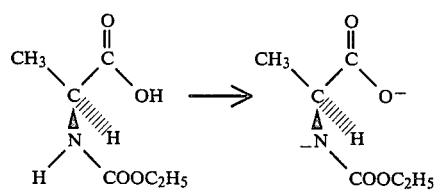

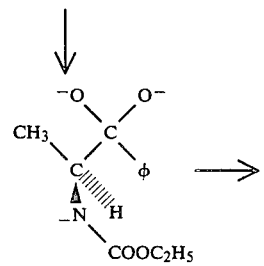

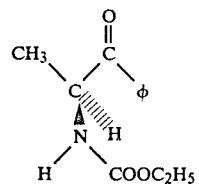

What seems to be happening is that if a complete generation of the dianion has not ensued, or is not possible, the carbomoyl carbonyl becomes a competitive site for attack. Protection of the asymmetry of the alpha-carbon also seems to stem from the successful generation of such a dianionic species. With two negatively charge centers adjacent to the chiral carbon, abstraction of the alphamethane proton is essentially prohibited. Hence, the presence of the abstractable carbamate proton facilitates ketone formation and protects the system totally from racemization.

Example VIII

In an attempt to eliminate the minor amount of nucleophilic attack on the carbonyl moiety which occurred even with slow, cold addition of phenyllithium, tertiary butoxycarbonylalanine was prepared. It was reacted with 300 mol percent of phenyllithium and afforded a modest yield of the desired ketone together with traces of the corresponding diphenyl carbonyl and the phenyl amino carbonyl. Tertiary butyl benzoate was not observed among the products. Decarbamoylation, however, had occurred, mediated by base abstraction of a beta proton as evidenced in the liberation of isobutylene.

Example IX

N-methoxycarbonylalanine was reacted under the same conditions as for the ethoxy analog and afforded the desired phenyl ketone. However, increased carbamoyl attack was observed. As a result, it was concluded that N-ethoxycarbonylalanine affords the most efficient ketone preparation with phenyllithium.

Example X

The significance of NH proton abstraction was further tested by treating N-benzenesulfonyl alanine with 300 mol percent phenyllithium to give an excellent yield of the phenyl ketone, evidently via the corresponding dianion. Subsequent reduction to N-benzosulfonyl amphetamine, followed by alkylation and detosylation, led to the desired N-methylamine. Diastereomer analysis of the latter confirmed that benzenesulfonyl amino acylation occurred without racemization. Thus, the benzenesulfonyl moiety proved to be an extremely useful protecting group in those reactions involving strong nucleophilic basis. The ease with which N-alkylation occurs lends further utility to this preparative path through which a large variety of optically pure secondary and tertiary amines are accessible.

REACTIONS OF N-ALKOXYCARBONYLALANINES WITH PHENYLMAGNESIUM BROMIDE

Example XI

The techniques which resulted in successful amido acylation of benzene using phenyllithium were next applied to the Grignard reaction. N-ethoxycarbonylalanine was treated with 300 mol percent of phenylmagnesium bromide at −78° C. and allowed to warm to room temperature. The desired ketone was not observed. Several hours of refluxing in ether and tetrahydrofuran yielded biphenyl and starting material which was optically intact.

Example XII

The previous example was repeated with the exception that the free acid was first converted to the acid chloride and 200 mol percent of phenyl magnesium bromide was utilized instead of 300 mol percent. This gave the desired ketone in very good yield together with a small quantity of biphenyl. The corresponding diphenylcarbonol was also formed in trace amounts.

Example XIII

The acid chloride experiment of the last example was repeated, with the exception that only 100 mol percent of phenyl magnesium bromide was utilized. No ketone was formed. However, when a second 100 mol percent of the Grignard reagent was added, the desired product resulted.

The above results suggest that the first step in the Grignard reaction involves an acid-base neutralization of the carbamate proton, thereby forming the oxazolinone. The second mol of Grignard evidently then attacks the oxazolinone carbonyl, leaving the ring system intact until aqueous hydrolysis liberates the desired ketone. It is believed that the magnesium cation strongly coordinates with the oxazoline, thus maintaining the integrity of the cyclized intermediate.

PREPARATION OF REAGENTS

The various N-substituted alpha-amino acid derivatives of the invention were generally prepared by conventional procedures. The following examples will make clear the preparation of several of the compounds which are useful in the practice of the present invention.

Example XIV

L-N-tosyl-N-methylalanine was prepared in 93% yield from N-methylalanine in the manner described by Greenstein, J. P. and Winitz, M. "Chemistry Of The Amino Acids", John Wiley and Sons, Inc., New York, 1961, Volume III.

Example XV

L-N-benzyloxycarbonyl-N-methylalanine was prepared in 71% yield from N-methylalanine by the method described in Volume II of the previously mentioned book "Chemistry Of The Amino Acids".

Example XVI

L-N-ethoxycarbonyl-N-methylalanine was prepared by th same method as L-N-benzyloxycarbonyl-N-methylalanine was prepared. A 75% yield of an oil was obtained.

Example XVII

L-N-tosylalanine was prepared in a 88% yield from L-alanine by the method described in Volume III of "Chemistry Of The Amino Acids".

Example XVIII

L-N-benzyloxycarbonylalanine was prepared in 70% yield by the same method as previously described for the carbobenzoxylation of N-methylalanine.

Example XIX

L-N-ethoxycarbonylalanine was prepared by addition of ethylchloroformate in 2 to 3 milliliter portions over a one hour period to a magnetically stirred solution of L-alanine and 1N NaOH at 15° C. Small portions of 1N NaOH were periodically added to maintain the pH in the range of 9 to 9.5. At the conclusion of the chloroformate addition and on stabilization of the pH at approximately 9.5, the reaction mixture was cooled to 0° C., extracted with ether and adjusted with cooling to pH 1 by addition of phosphoric acid. The aqueous phase was then saturated with sodium chloride and extracted with $CH_2Cl_2$ and the combined organic phases were evaporated to given an 85% yield of the desired product of a clear light yellow oil.

Example XX

To a magnetically stirred solution under nitrogen at 0° C. of L-N-ethoxycarbonylalanine (16.1 gram) in $CH_2Cl_2$ (300 ml) was added 0.5 ml of DMF and 10 ml of oxalyl chloride in one portion. The reaction mixture was allowed to warm to room temperature and after 1.5 hours was diluted with $CH_2Cl_2$ (150 ml) and benzene (1250 ml) and cooled to −15° C. In one portion $AlCl_3$ (28.4 gram) was added and stirring was continued at −15° C. for 12 hours. The homogeneous solution was quenched with cold 1N HCl (300 ml), diluted with cold water (200 ml), the phases separated, and the organic layer washed successively with cold 1N HCl (two 300 ml portions), water (300 ml) and saturated $NaHCO_3$ (two 300 ml portions). Evaporation of the organic phase afforded an oil which was crystallized by tritrating in warm hexane and cooling overnight at 0° C. to yield 19.9 gram (90%) of the desired product.

Example XXI

N-t-butyloxycarbonylalanine was prepared in 85% yield by the method of Moroder, L., et al, Z. Physiol. Chem., 1976, 357, 1651.

Example XXII

N-methoxycarbonylalanine was prepared by the same method that N-ethoxycarbonylalanine was prepared. A 61% yield was obtained.

Example XXIII

N-benzenesulfonylalanine was prepared by mixing equimolar quantities of alanine and benzenesulfonyl chloride at 60° C. in aqueous sodium hydroxide (200 mol%). A 95% yield was obtained. The method is set out in the previously mentioned book "Chemistry Of The Amino Acids".

INDUSTRIAL APPLICABILITY

The invention operates to provide novel optically active alpha-amino acid derivatives which can have the acid portion thereof converted into a ketone functionality with substantially complete retention of optical asymmetry. The ketone can then be further reacted, generally by reduction, to form medicinally useful substances such as ephedrines, amphetamines, and the like. Since racemization does not occur during the reactions, the need for separation of mixed optical isomers is eliminated.

We claim:

1. A method of preparing an alpha-amino alkyl organic ketone having an asymmetric alpha carbon atom, comprising reacting a compound having an asymmetric alpha carbon atom, said compound having the formula:

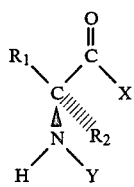

wherein X is OH, Cl, Br, or $OCOR_3$;

Y is a radical selected to stabilize the alpha carbon atom of the alpha-amino acid derivative sufficiently to prevent significant change in symmetry thereof during replacement of X with an alkyl, aryl, alkenyl, alkynyl, alkarly, aralkyl, alkenaryl or alkynaryl radical, or such radical having one or more chemical constituents thereon, Y being selected from $-SO_2R_4$; $-SeO_2R_4$; $-TeO_2R_4$; $-PO_3R_4$;

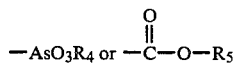

wherein $R_4$ is hydrogen, an alkyl, aryl, alkenyl, alkynyl, alkaryl, aralkyl, alkenaryl, alkynaryl radical, or such radical having one or more non-protic chemical constituents thereon, or is one or more non-protic chemical constituent; and $R_5$ is an alkyl, aryl, alkenyl, alkynyl, alkaryl, aralkyl, alkenaryl or alkynaryl radical, or such radical having one or more non-protic chemical constituent;

$R_1$ and $R_2$ are different from one another and are each hydrogen or an alkyl, aryl, alkenyl, alkynyl, alkaryl, aralkyl, alkenaryl, or alkynaryl radical, or such radical having one or more non-protic chemical constituents thereon; and $R_3$ is hydrogen, or an alkyl, aryl, alkenyl, alkynyl, alkaryl, aralkyl, alkenaryl, or alkynaryl radical or such a radical having one or more chemical constituents thereon; with a reagent capable of converting the

portion of said compound to said ketone, either said reacting being via a Friedel-Crafts reaction and said reagent being aromatic or said reacting being via an organometallic reaction and said reagent being an organometallic reagent, said ketone substantially retaining the stereospecificity of said compound at said alpha carbon atom.

2. A method as set forth in claim 1, wherein said reagent is aromatic and said reacting is via a Friedel-Crafts reaction.

3. A method as set forth in claim 2, wherein X is Cl, Y is $CO_2C_2H_5$ and $R_2$ is hydrogen.

4. A method as set forth in claim 1, wherein said reagent is an organometallic reagent.

5. A method as set forth in claim 4, wherein said organometallic reagent is an organomagnesium halide and said reacting is via a Grignard reaction.

6. A method as set forth in claim 4, wherein said organometallic reagent is an organolithium reagent.

7. A method as set forth in claim 1, wherein said compound is substantially optically pure and said ketone is substantially optically pure.

8. A method as set forth in claim 1, wherein Y is

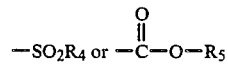

* * * * *